(12) United States Patent
Sakas et al.

(10) Patent No.: US 7,412,086 B2
(45) Date of Patent: Aug. 12, 2008

(54) SETTING A RELATIVE POSITION OF A RADIATION DEVICE AND A PATIENT

(75) Inventors: Georgios Sakas, Darmstadt (DE); Boris Peter Selby, Mosbach (DE); Stefan Otmar Walter, Darmstadt (DE); Rolf Kussäther, Darmstadt (DE)

(73) Assignee: Medcom Gesellschaft fur Medizinische Bildverarbeitung mbH, Darmstadt (DE)

( * ) Notice: Subject to any disclaimer, the term of this patent is extended or adjusted under 35 U.S.C. 154(b) by 604 days.

(21) Appl. No.: 11/206,116

(22) Filed: Aug. 18, 2005

(65) Prior Publication Data

US 2006/0058620 A1    Mar. 16, 2006

(30) Foreign Application Priority Data

Aug. 19, 2004    (DE) .................. 10 2004 040 629

(51) Int. Cl.
*G06K 9/00*    (2006.01)
*A61N 5/10*    (2006.01)

(52) U.S. Cl. .................. 382/131; 378/65; 378/98.5; 250/492.1; 250/492.3; 600/427; 600/429

(58) Field of Classification Search .................. 382/131, 382/128; 600/427, 429, 407; 250/492.1, 250/492.3
See application file for complete search history.

(56) References Cited

U.S. PATENT DOCUMENTS

| | | | | |
|---|---|---|---|---|
| 6,052,611 | A * | 4/2000 | Yanof et al. ................. | 600/429 |
| 6,219,403 | B1 * | 4/2001 | Nishihara .................... | 378/65 |
| 6,804,548 | B2 * | 10/2004 | Takahashi et al. ........... | 600/427 |
| 7,280,633 | B2 * | 10/2007 | Cheng et al. .................. | 378/65 |
| 2003/0233123 | A1 * | 12/2003 | Kindlein et al. ............... | 607/2 |

FOREIGN PATENT DOCUMENTS

| | | |
|---|---|---|
| DE | 3436444 | 4/1986 |
| DE | 10147633 | 7/2002 |

OTHER PUBLICATIONS

Oct. 4, 1986, Roettinger, Abstract of DE3436444.

* cited by examiner

*Primary Examiner*—Andrew W. Johns
*Assistant Examiner*—Nancy Bitar
(74) *Attorney, Agent, or Firm*—Neifeld IP Law, PC

(57) ABSTRACT

A method and arrangement for setting a relative position of a radiation device and a patient. The invention relates to the use of radiation therapy for the targeted, selective destruction of tumors.

7 Claims, 4 Drawing Sheets

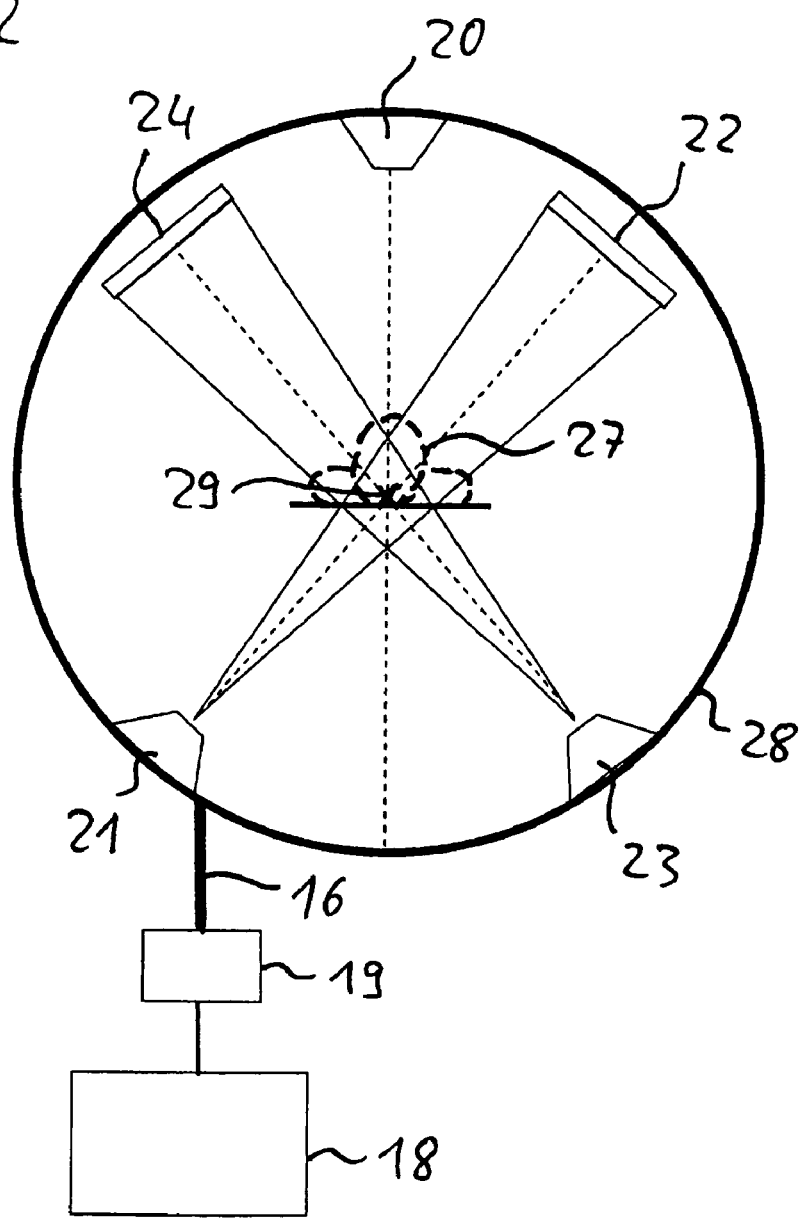

a      b      c      d

SETTING A RELATIVE POSITION OF A RADIATION DEVICE AND A PATIENT

Figure 1:
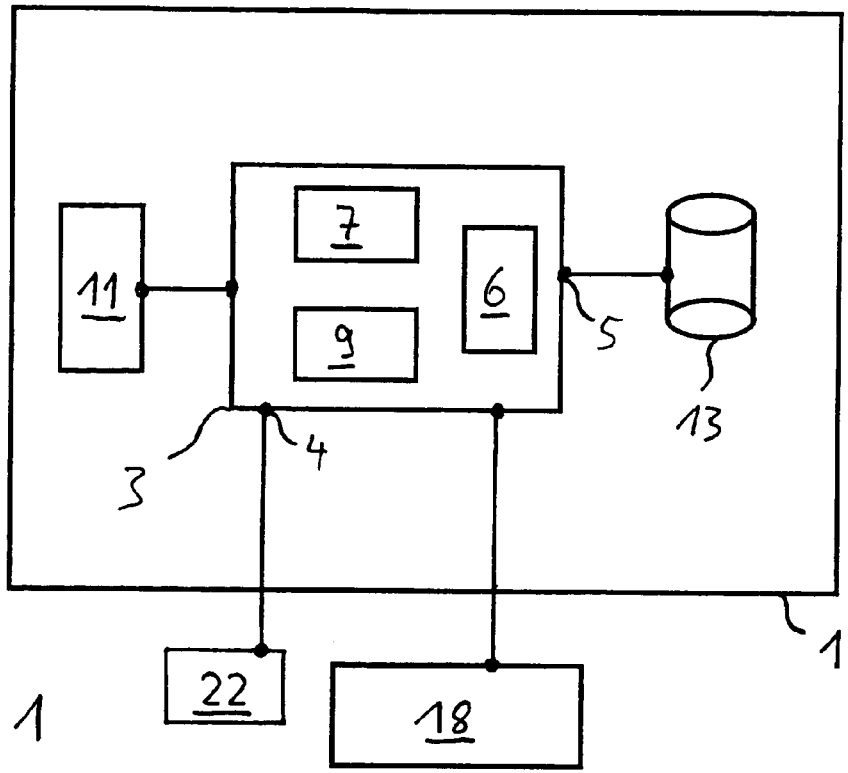

This application claims priority to German application DE 10 2004 040 629.4, filed on Aug. 19, 2004. The foregoing application DE 10 2004 040 629.4 is hereby incorporated by reference.

The invention relates to a method and an arrangement for setting a relative position of a radiation device and a patient. In particular the invention relates to the use of radiation therapy for the targeted, selective destruction of tumours. This description refers in full to the German patent application with the reference DE 10 2004 040 629.4, filed on 19 Aug. 2004, and incorporates its content.

Photons (e.g. X-rays) are predominantly used for the radiation of patients. However, an innovative development enables proton beams to be used in order to destroy the malignant tissue. High-resolution pictures of the region of the patient to be treated can be used in planning the radiation treatment and a corresponding three-dimensional image data set can be stored. Three-dimensional image data of this type are preferably obtained by means of a computer tomography (CT) method or a magnetic resonance (MR) method. The doctor is then able to evaluate the high-resolution image data using computer-supported image processing techniques. After the doctor has completed the planning of the radiation the patient is treated with the radiation device.

In order to enable the radiation to be carried out as planned, the patient must be positioned as precisely as possible relative to the radiation device. A very small error in positioning leads to the destruction of healthy tissue and/or to inadequate radiation of the tumour tissue.

Therefore, for example, a two-dimensional comparison image can be taken and used for further invasive radiation (e.g. X-rays). The comparison image can now be compared with a two-dimensional reconstructed image, reconstructed from the locally three-dimensional image data set of the patient. This enables errors in the current position of the patient to be determined and corrected. In particular it is possible, that the reconstructed image simulates an image taken with the comparison image recording device. Thus the reconstructed image corresponds to an assessed or assumed relative position of the patient and the comparison image recording device. Such reconstructed images can be, for example, so-called DRRs (Digitally Reconstructed Radiographs).

Due to the large quantity of data involved in the high-resolution image data it is very expensive in terms of time to systematically compare images reconstructed from various angles of view and along various viewing directions with the comparison image. The longer the wait before the radiation treatment can commence or be continued, the greater is the probability, that the position of the area to be radiated will have changed again and for this reason the position correction determined from the comparison will be false. Also, the costs of radiation treatment depend on its duration. Therefore costs can be saved if the time taken to position the patient can be reduced.

In order to reduce the computation time, the resolution of the image data used for the comparison can be intentionally reduced. But this results in a loss of accuracy in the positioning.

For this reason methods have already been suggested, which are oriented on uniquely recognisable structures in the body of the patient (e.g. the outlines of bones) or on artificial markers associated with the patient's body (so-called natural and artificial landmarks). These methods enable the time required to compare images to be reduced, since it is only necessary to find known structures in parts of the images. However, the less well-defined the structures to be found (e.g. the visible edges of round bones, which are not very sharply defined in two-dimensional images) the less precise is the positioning of the patient. Also, the structures in the comparison image and in the reconstructed image are represented differently if the three-dimensional image data and the comparison images have been derived using different image recording methods. In addition, in many cases, there is no clearly recognisable structure in the images in the vicinity of the area to be radiated. The greater the distance between the landmarks and the area to be radiated the less accurate is the result of the positioning.

It is therefore a task of the present invention to provide a method and an arrangement of the type named in the introduction, which enables an exact positioning of the patient relative to the radiation device to be determined in the shortest possible time. Herein, it should be possible for the radiation target to be positioned in any arbitrary area in the body of a patient. In particular, it should be possible to use different methods of imaging to obtain the comparison images and the three-dimensional data set relating to the patient.

A method is suggested for setting a relative position of a radiation device and a patient, in which the following steps are carried out:

a) At least one locally two-dimensional comparison image is used in each case, wherein the comparison image is obtained, or has been obtained, with a comparison image recording device and wherein the comparison image corresponds to a current relative position of the patient and of the comparison image recording device.

b) Reconstructed locally two-dimensional images (reconstructed images) from a locally three-dimensional image data set of the patient are used, wherein the reconstructed images simulate, for example, at least a part of an image taken with the comparison image recording device, which image corresponds to an estimated or assumed relative position of the patient and of the comparison image recording device.

c) For a comparison image and a first reconstructed image, which form a first image pair, a measure is determined for the mutual image information of the two images of the first image pair, wherein the mutual image information is defined as that information, which one image contains about the other image, or wherein the mutual image information is equivalent to the thus defined information.

d) The comparison image and/or the reconstruction image are amended, without distortion of the image content, so that at least one of the images corresponds to another relative position of the patient and of the comparison image recording device, (first variant) and/or a second reconstructed image is reconstructed from the locally three-dimensional image data set of the patient, so that the second reconstructed image and the first reconstructed image correspond to a second and a first relative position of the patient and of the comparison image recording device (second variant).

e) The measure for the mutual image information for the two images resulting from step d) is re-determined.

f) The two previous steps d) and e) are repeated using an optimisation algorithm, until a maximum is found for the mutual image information for a corresponding resulting image pair.

g) By evaluating the changes in the relative position of the patient and of the comparison image recording device in the images, which arise, or have arisen, starting from the first image pair and proceeding until the resulting image pair is discovered, a geometrical transformation of the actual relative position of the patient and of the comparison image recording device or of another actual relative position or position of the patient is calculated and h) Steps c) to g) are repeated, wherein the first reconstructed image is selected, such that it corresponds to the relative position or position as modified by the calculated geometric transformation.

With the locally three-dimensional image data set information is available on the inside of the patient, in particular information on the arrangement, size and structure (including any pathological changes) of the organs of the patient. Accordingly, the comparison images can be taken by the use of invasive radiation, e.g. with X-rays, which penetrates the patient or a part of the patient.

The reconstructed images simulate at least a part of an image taken with the comparison image recording device. This image is a hypothetical image, which only matches the actually taken image of the comparison image recording device when the positioning of the patient is completed without any remaining positional inaccuracies. In particular, the reconstructed images can be generated in such a way, that the actually recorded images are the same size or even smaller. In determining the mutual image information of the comparison image and the reconstructed image, preferably merely the parts of the images, which overlap each other, are considered.

By position or relative position of non-punctiform objects (e.g. of a patient) is meant a position, which is defined with reference to all degrees of freedom of the motion of the body, which is assumed to be rigid, or with reference to all degrees of freedom of the relative motions of both objects (radiation device and patient). In practice, additional changes to the objects take place with respect to time. In particular, it is routine that changes in the position, structure and/or form of the organs of the patient take place. For this reason it is preferable that smaller partial volumes of the patient are considered as the object.

Before the treatment commences, an optional pre-positioning of the patient can take place. In this case the patient is pre-positioned, for example on a treatment chair or treatment table. Aids such as fixation masks and/or fixation mattresses can be used. Also, positioning systems (sometimes with the use of laser radiation) can be used, which evaluate information on the outer surface of the patient. For example, markers applied to the skin are used, whose positions are determined using a tracking system.

In step c), for a comparison image and a first reconstructed image, which form a first pair of images, a measure is determined for the mutual image information from the two images of the first image pair. In this the mutual image information is defined as that information, which one image contains about the other image, or is equivalent to the mutual image information of the thus defined information. An example of the determination of the mutual information of three-dimensional image data sets and the usage of the information for the registration of the image data sets is described in the article "Comparative evaluation of multi-resolution optimization strategies for multi-modality image registration by maximization of mutual information" by Frederik Maes et al., "Medical Image Analysis" (1999) volume 3, number 4, pages 373-386. However, the difference in this present solution is that here two-dimensional images are compared with one another and the mutual image information is determined.

The application of the method of mutual image information for the evaluation of the agreement between the comparison image and the reconstructed image has the advantage that the images do not have to be obtained by the same method. One reason for this lies in the fact that maximum match can only be found if the image structures are not identical.

In step d) the comparison image and/or the reconstructed image are modified without distortion of the image contents (for example, by a rotation about an axis at right angles to the plane of the image and/or by a shift in the plane of the image). The positioning error can be reduced in this way by finding the image pair with the maximum mutual information (step f) and calculating the geometrical transformation of the actual relative position or position. For example, the geometrical transformation is thus determined merely by a shift along the coordinate axes in the plane of the reconstructed image and/or by the angle of rotation about the axis of rotation at right angles to the plane of the image.

Alternatively or additionally, in step d) a second reconstructed image is reconstructed from the locally three-dimensional image data set of the patient, so that the second reconstructed image and the first reconstructed image correspond to a second and a first relative position of the patient with respect to the comparison image recording device. A difference here compared with the previously described variant is that a new reconstructed image is calculated. So that during the optimisation carried out in step f) preferably merely one degree of freedom is permitted (In particular a rotational degree of freedom, i.e. one degree of freedom of a rotary motion about an axis of rotation). In other words, in this way preferably the image pair is found, which provides the best match when merely those geometric transformations are permitted, which correspond to the one degree of freedom. Then the geometrical transformation is calculated in step g). In this way, for example, merely the value of the rotation about the axis of rotation corresponding to the image pair providing the best match is read out from a data memory. This value has already been determined in order to form the image pair in the corresponding iteration in step d).

A difference between the two variants in step d) is thus, that in the first variant the areas of the image in the comparison image and in the reconstructed image, which match each other regarding their proportions, can be used for congruence. On the other hand, the image contents in the respective image pairs in accordance with the second variant in step d) can differ fundamentally. Thus the correction of the position error can be carried out in a simple manner by repeating steps c) to g) with respect to different degrees of freedom of the translation and the rotation, in which in at least one execution of the steps c) to g) one variant of step d) is selected and in at least one other execution the other variant of step d) is selected. At the same time the degrees of freedom are at least partly decoupled from one another, by which means the total time required for the execution of the procedure is again reduced.

However, in both variants, information on how the error in the positioning of the patient relative to the three-dimensional data set (i.e. the registration) can be improved is available at the end of step g).

Examples of the optimisation algorithm used in step g) are described in the publication by F. Maes et al. referred to above.

The evaluation of changes in the relative position in step g) is also taken to imply an indirect evaluation of the relative position in which, for example, merely the change in position of a treatment device on which the patient is supported, e.g. a treatment table on which the patient is lying, is evaluated. Alternatively or additionally, the change in position of the radiation device and/or of an associated device (for example a moving wall of a treatment chamber) can be evaluated.

Accordingly, the calculated geometrical transformation can relate to the change of position of one or more of the named devices.

However, there is a basic recognition in respect of the invention, that as a rule a once only execution of the iteration completed at step g) does not provide the best result for the geometrical transformation used in the correction of the position error.

This particularly applies to cases, in which a rotation of the patient about an axis of rotation (or an equivalent transformation) is required as a correction, in which the axis of rotation is at right angles to the plane of the image of the comparison image (i.e. runs parallel to the plane of the image or in the plane of the image) and in which the image pairs have been varied in accordance with the first variant in step d). A basis for this is that a rotation about this axis of rotation in the first variant in step d) leads to modified image contents in the reconstructed image. Here a yet closer approximation will be obtained with reference to an inserted figure. Since the comparison image has been taken with invasive radiation and therefore an image plane is not initially defined, the plane of a device taking the comparison image, or a plane parallel with it in the middle between the device taking the image and a source of radiation can, for example, be described as the plane of the image.

Furthermore, in step g) merely a locally maximum of the mutual information can be determined, which is, however, not the absolute maximum.

Therefore, in accordance with the invention, steps c) to g) are repeated, in that the first reconstructed image for the repetition is selected such that it corresponds to the relative position or position as modified by the calculated geometrical transformation. In the case of multiple repetitions of steps c) to g) the calculated geometrical transformation employed is preferably the total calculated geometrical transformation from all the previous executions of steps c) to g).

Consequently, the repetitions of steps c) to g) are obtained from a relative position of the patient and of the radiation device, which is the result of the found geometrical transformation. At least at the commencement of the repetition of steps c) to g) a new reconstructed image is determined, so that locally maxima of the mutual information can be suppressed and the actual absolute maximum of the mutual information can be found. In this process, each of the repetitions in steps c) to g) can be executed in a short period of time on the basis of the optimisation algorithm (e.g. a Downhill-Simplex-Algorithm). Overall the suggested method is therefore essentially faster in its execution than a systematic comparison of all possible reconstructed images with the comparison image.

One version of the method according to the invention utilises the second variant in step d), in which the second relative position (i.e. the relative position, which corresponds to the new reconstructed reconstructed image) can be transferred to the first relative position (i.e. this is the relative position, which corresponds to the earlier reconstructed image) through a rotational motion of the patient about a defined axis of rotation. This version has already been mentioned above as an example. Furthermore, a respective further reconstructed image can be reconstructed from the locally three-dimensional image data set of the patient, preferably in connection with a repeat of steps d) and e), in order in step f) to find the image pair with the maximum of the mutual image information by using an optimisation algorithm, so that the further reconstructed image corresponds to a further relative position of the patient and the comparison image recording device, and wherein the further relative position can be transferred to the first relative position through a rotational motion of the patient about the defined axis of rotation. Thus in simple terms, the iterations provide a means of comparing a plurality of reconstructed images with the comparison image and of determining the reconstructed image providing the closest match. However, since there is only one degree of rotational freedom, the image pair with the best match is quickly identified. Tests have shown, that the result is stable and is not considerably dependent on other degrees of freedom of the translation and rotation if the axis of rotation runs parallel to the image plane of the comparison image. Therefore, as a rule one execution of steps d) to f) in accordance with this version is adequate.

In a preferred version of the method a measure for the mutual image information of the comparison image and of the assigned reconstructed image (image pair) is determined in step c) for two comparison images, which respectively have been taken by a comparison image recording device, and for the reconstructed images assigned to the respective comparison images. In this procedure the comparison image recording devices take the comparison images of the patient from different directions. Then in step d) the comparison image and/or the reconstructed image are modified for both image pairs (e.g. through a rotation about an axis at right angles to the image plane and/or through a shift in the image plane), so that at least one of the images corresponds to another relative position of the patient and the comparison image recording device. Steps e) and f) are carried out separately for both image pairs. In the execution of step g) the optimisation results from step f) are taken into consideration for both image pairs.

In particular, in this version the comparison image recording devices can take comparison images of the patient, in which procedure the image recording directions (e.g. the mid perpendicular to the planes of the image) are perpendicular (or almost perpendicular) to the same axis of rotation. Position corrections due to rotational movement about this axis of rotation are in this case determined from neither of the two comparison images, since the corresponding position errors are merely perceptible due to distorted image contents. Then in the execution of step g) the calculated geometrical transformation is iteratively improved by repeating the calculation.

An example of this version will be described with reference to the attached drawing. The use of two comparison image recording devices enables the results obtained with the two comparison images to be compared with one another to verify the results. This increases the accuracy. In addition, correction of the position errors in respect of several degrees of freedom can be determined in a particularly short time.

Further, an arrangement for the adjustment of a relative position of a radiation device and a patient is suggested, in which an image data evaluation device is provided, which is connected to an interface for the transfer of image data, wherein the image data evaluation device is devised to process at least one locally two-dimensional comparison image and reconstructed images, wherein the comparison image is obtained or has been obtained with a comparison image recording device by the use of invasive radiation and wherein the comparison image corresponds to a current relative position of the patient and the comparison image recording device, wherein the reconstructed images from a locally three-dimensional image data set of the patient are reconstructed locally two-dimensional images, wherein the respective reconstructed images simulate at least a part of an image taken with the comparison image recording device, which corresponds with an estimated or assumed relative position of the patient and the comparison image recording device, the image data evaluation device has a determination device, which for a comparison image and a first reconstructed image, which form a first image pair, is devised to determine a measure for the mutal image information of both images of the first image pair, wherein the mutual image information is defined as that information, which one image contains about the other image, or wherein the mutual image information is equivalent to the thus defined information, the image data evaluation device has an imaging processing device, which is devised to modify the comparison image and/or the reconstructed image without distortion of the image content, so that at least one of the images corresponds to another relative position of the patient and the comparison image recording device, and/or which is devised to reconstruct a second reconstructed image from the locally three-dimensional image data set of the patient, so that the second reconstructed image and the first reconstructed image correspond to a second and a first relative position of the patient and the comparison image recording device, a control device is provided, which is connected to the determination device and the image processing device and which is devised to control the operation of the determination device and the image processing device, in such a way, that repeatedly for an image pair made provided by the image processing device, a measure for the mutual image information is determined and using an optimisation algorithm a maximum is found for the mutual image information for a corresponding resulting pair of images, a transformation calculation device is provided for the evaluation of changes to the relative position of the patient and the comparison image recording device corresponding to the images, which arise or have arisen proceeding from the first image pair up to the point of finding the resulting image pair, wherein the transformation calculation device is devised to calculate a geometrical transformation of the actual relative position of the patient and the comparison image recording device or another actual relative position or position of the patient, wherein the control device is devised to control the operation of the arrangement in such a way, that commencing from a newly calculated first reconstructed image and for the corresponding comparison image the geometrical transformation is calculated, wherein for the corresponding comparison image the geometrical transformation is repeatedly calculated, wherein the first reconstructed image is selected, such that it corresponds to the relative position or position as modified by the calculated geometrical transformation.

In particular, the arrangement can have an image data memory, in which the three-dimensional image data set is stored, wherein the image data memory is connected to the image data evaluation device.

The advantages and forms of the arrangement are evident from the foregoing description of the method according to the invention.

Further, a computer program is included in the scope of the invention, which when used on a computer or computer network executes the method according to the invention in its different versions.

In addition, a computer program with a computer program means is included in the scope of the invention in order to carry out the method according to the invention in one of its various versions when the program is executed on a computer or computer network. In particular, the computer program means can be stored on a data carrier readable by a computer.

Further, a data carrier is included in the scope of the invention, on which a data structure is stored, which after loading in a working and/or main memory of a computer or computer network is able to execute the method according to the invention in one of its various versions.

Also belonging to the invention is a computer program product with a computer program means, which is stored on a machine-readable carrier, in order to carry out the method according to the invention in one of its versions when the program is executed on a computer or computer network.

By computer program product is meant the program in the form of a marketable product. It can exist in any arbitrary form, for example on paper or on a computer-readable data carrier and, in particular, it can be distributed via a data transfer network.

The invention is described in detail in the following on the basis of example versions, which are represented schematically in the figures. However, the invention is not restricted to the examples. In the individual figures the same reference numbers indicate the same or functionally similar elements or similar elements in respect of their function with other elements. The following features are shown:

FIG. 1 A particularly preferred arrangement for setting a relative position of a patient and a radiation device.

FIG. 2 A cross-section through an arrangement for the radiation treatment of a patient.

Figure 3:
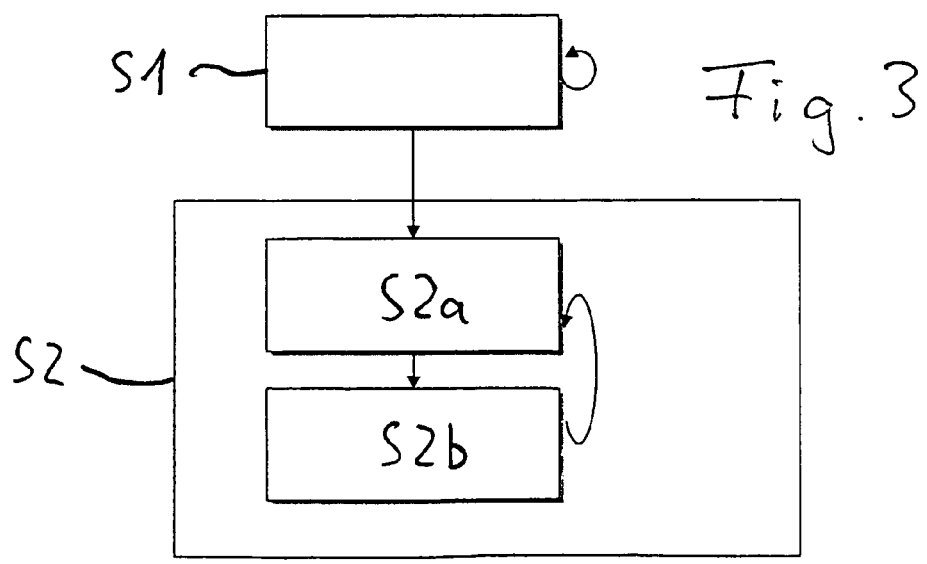

FIG. 3 A flow diagram for the representation of one form of the method according to the invention, which corresponds to the best version.

Figure 4:
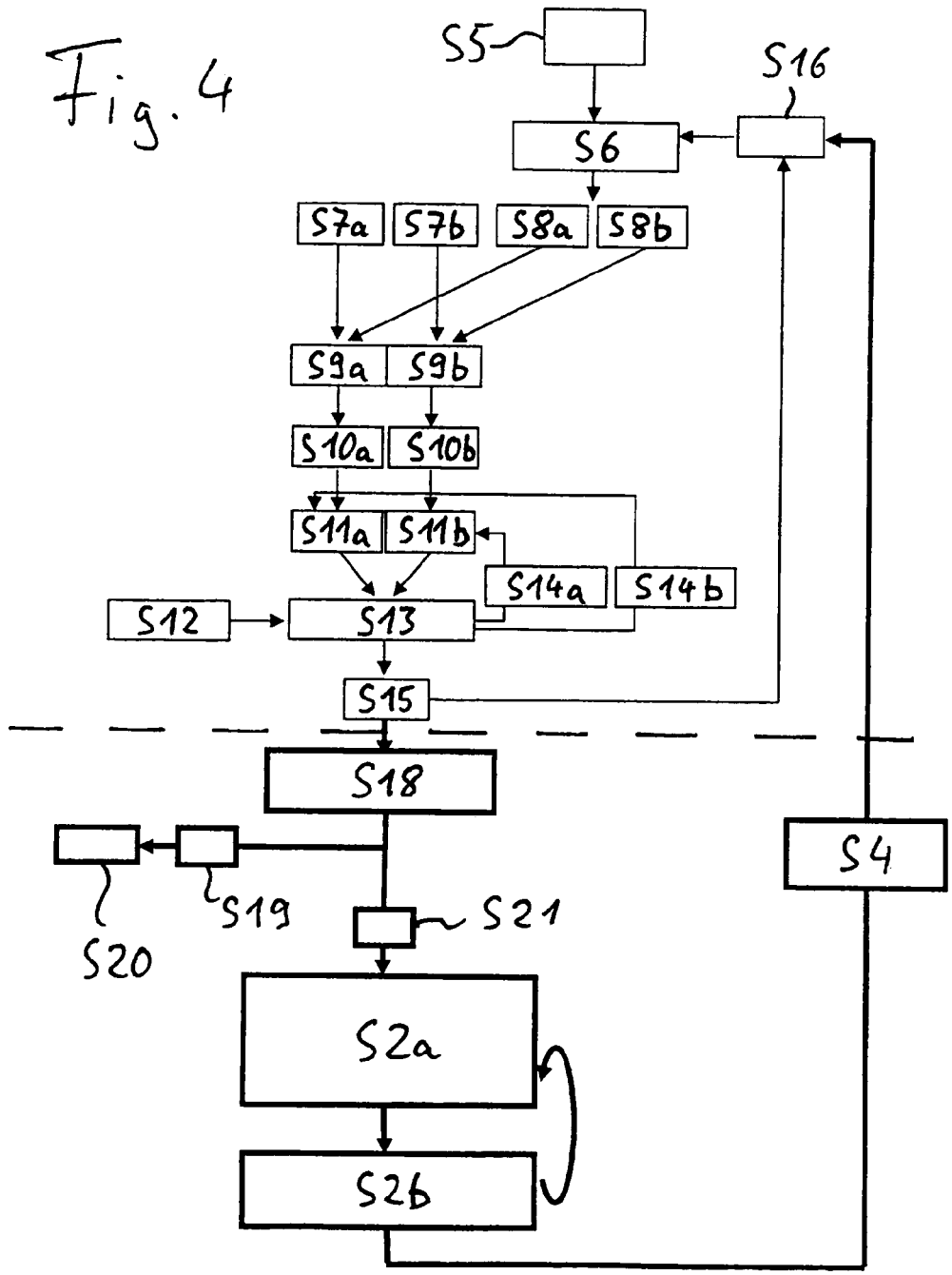

FIG. 4 A flow diagram for one version of the method represented in FIG. 3.

Figure 5:
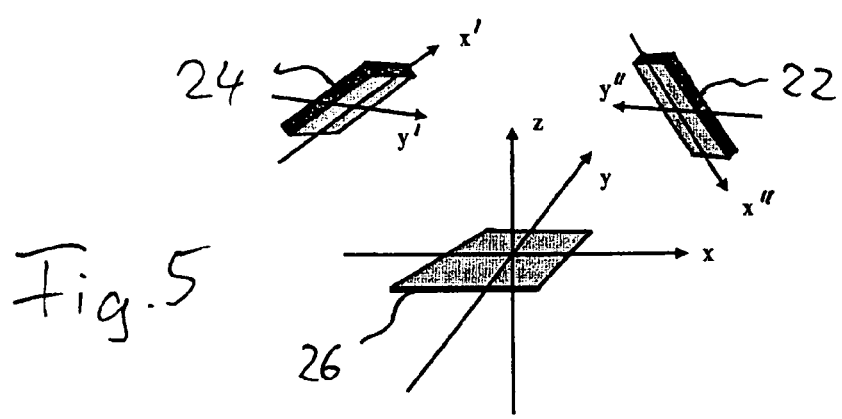

FIG. 5 Parts of the treatment arrangement represented in FIG. 2 with the associated coordinate system.

Figure 6:
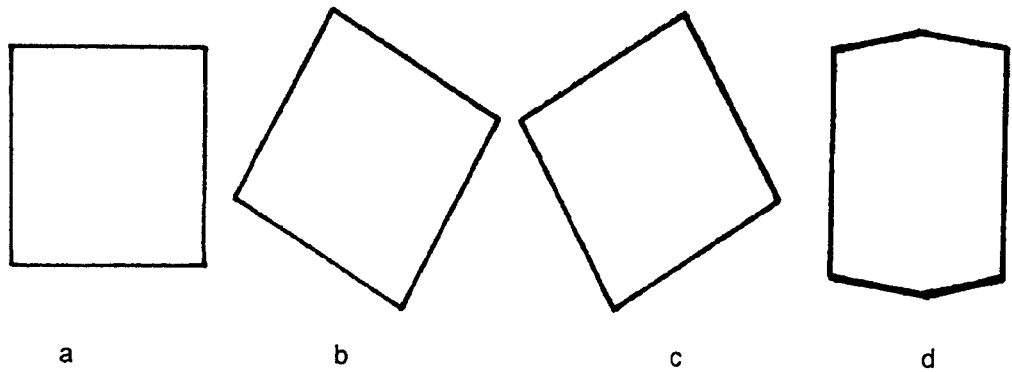

FIG. 6 Four reconstructed images, which can be transformed into each other by rotations about an axis of rotation.

FIG. 1 shows an arrangement 1 with an evaluation device 3, which is connected to a control device 11. The evaluation device 3 is connected to an image data memory 13 and has a determination device 6, an image processing device 7 and a calculation device 9. Outside the arrangement are an additional control device 18 for the adjustment of the relative position of the patient and of a radiation device and a first image recording device 22 to take a comparison image. The control device 18 and the first image recording device 22 are connected to the evaluation device 3. Other image recording devices can be provided to take additional comparison images.

The arrangement 1 shown in FIG. 1 is achieved, for example, by means of a normal commercially available computer, in particular a Personal Computer (PC). The devices 6, 7, 9, and 11 can be fundamentally realized through hardware and/or software.

The evaluation device 3 receives image data of a three-dimensional image data set of the patient from the image data memory 13 via the interface 5 and from it calculates two-dimensional reconstructed images (e.g. in the image processing device 7). From the first image recording device 22 the evaluation device 3 receives image data of a comparison image via an interface 4. The determination device 6 determines a measure for the mutual information of the images for a comparison image and a related reconstructed image, respectively. The image processing device 7 generates new image pairs or partial images of image pairs, for which the determination device 6 again determines the measure for the mutual information. Under the control of the control device 11 a respective image pair with maximum mutual information is determined, wherein the calculation device 9 determines correction parameters for this image pair, which define a correction of the relative position of the patient and the radiation device. The control device 11 also controls the operation of the evaluation device 3, so that commencing with a new image pair, which is created using the correction parameters, an image pair with maximum mutual information is determined. This procedure can be repeated once or plural times. As a result, at the end of the iteration optimized correction parameters are available. The relative position is then corrected through the output of appropriate signals to the control device 18.

From the cross-section shown in FIG. 2 of the treatment arrangement a tube-like treatment chamber with a wall 28 can be seen (The so-called gantry). The tube is positioned perpendicular to the plane of FIG. 2 and has an approximately constant cross-section. In one version of the treatment chamber, a radiation device 20, devised for example as a proton radiation device, two image recording devices 22, 24 and radiation sources 21, 23, respectively, assigned to the image recording devices 22, 24 are provided, which can all be connected to the wall 28. In this way it is possible to undertake a correction of the relative position, such that the wall is moved (In particular rotated about its central longitudinal axis 29 as the axis of rotation). However, the same correction of the relative position can also be achieved by appropriate rotation of a treatment table 26, arranged in the treatment chamber, on which the patient 27 is positioned. The treatment table 26 can also be moved with respect to other degrees of freedom in order to facilitate the correction of the position. The position correction is controlled by the control device 18 (As shown schematically in FIG. 2) and carried out by the use of at least one motor 19, which is connected via a drive 16 to the respective moving part of the treatment arrangement.

The radiation sources 21, 23 each have an X-ray tube, for example. The first radiation source 21 is assigned to the first image recording device 22. The radiation originating from the first radiation source 21 penetrates the patient 27 and, appropriately weakened, strikes the first image recording device 22. A comparison image is obtained by this means, in particular an X-ray image. The second radiation source 23 and the second image recording device 24 are correspondingly arranged and devised. E.g. the centre point rays of the radiation originating from the radiation sources 21, 23 lie in a common plane, which is perpendicular to the longitudinal axis 29 of the treatment chamber. The centre point rays run obliquely to each other, but preferably not perpendicular to each other. If the centre point rays are perpendicular to each other, additional expense is necessary in the evaluation of the comparison of the image pairs, as will be explained in greater detail in an example version of the method according to the invention.

With reference to FIG. 3 a particularly preferred version of the method according to the invention will now be described. In a step S1, commencing with at least one image pair, which comprises a comparison image and a reconstructed image, a modified image pair is determined in respect of the relative position, whose mutual information is a maximum. In this procedure no distortions of the image contents is permitted in obtaining a new image pair. Consequently a position correction is determined, which can be exclusively described by displacements in the plane of the reconstructed image and/or by a rotation about an axis of rotation perpendicular to the plane of the image. As shown by a curved arrow, step S1 is preferably repeated until an optimized result is established for the position correction. If two comparison images are available, step S1 can be carried out in parallel for both comparison images and the results can be compared with each other, for example in that the position corrections are transposed into a common coordinate system (e.g. the coordinate system of the patient). As a rule the results will not be exact agreement, so that an error or a deviation of the results can be calculated. In this case step S1 is carried out until the error is equal to or less than a previously defined error limit value.

Position corrections are now calculated in respect of at least one other axis of rotation, namely an axis of rotation, which is in the image plane of the comparison image or parallel to the image plane. As can be seen from FIG. 6, such position corrections are not reliably determinable if (As in step S1) no distortion of the image content is permitted or no new reconstructed images with modified image content are calculated. In FIG. 6 the outer frames of four images are represented. The image designated a is a first reconstructed image. The three other images in FIG. 6 have been generated from image a by rotation about various axes of rotation. Reference should be made to FIG. 5 for an explanation of the position of the axes of rotation relative to the plane of image a. FIG. 5 shows the treatment table 26 from FIG. 2 or another device, on which the patient is positioned. The coordinate system of the device 26 is represented by the coordinate axes x, y and z. The coordinate systems of the image planes of the first image recording device 22 (Coordinate axes x" and y") and of the second image recording device 24 (Coordinate axes x" and y") are also represented. The axis of rotation, about which the image b in FIG. 6 is rotated relative to the image a, is the x axis of the coordinate system of the device 26. It can be seen for image b, that the image content is only minimally distorted relative to the image content of image a, since the x axis is at right angles to the image plane of the first image recording device 22. The same applies to image c, which has been generated from image a by rotation about the z axis. Both the x axis and the z axis are likewise transverse to the image plane of the second image recording device 24. On the other hand, the y axis is parallel to the image plane of the first image recording device 22 and parallel to the image plane of the second image recording device 24. The image d has been generated from image a by rotation about the y axis. The image content of image d is significantly distorted relative to the image content of image a Conversely, it can be concluded, that position corrections in respect of rotations about the x axis and about the z axis can be determined from Step S1 and the same applies to displacements in the y direction. However, rotations about the y axis cannot be determined from Step S1.

If only one image recording device is available, two axes of rotation exist, which are at right angles to each other and are parallel with the image plane of the image recording device. In this case Step S2 is carried out to determine the position error in respect of the two corresponding degrees of freedom.

However, in the case of two image recording devices, whose normals are at right angles or are skewed relative to each other, the execution of Step 2 is adequate in respect of one degree of freedom of the rotation (i.e. in respect of the defined axis of rotation—in the case of FIG. 5 the y axis). This case is described in the following.

First, in Step S2a a reconstructed image is calculated, wherein first the position correction determined in Step S1 has been carried out. Then in the following Step S2b the measure for the mutual image information for the reconstructed image and the comparison image is determined for at least one of the image recording devices. Steps S2a and S2b are repeated using an optimisation algorithm, until an image pair is found with the maximum mutual image information. Here, in Step S2a, exclusively a rotation about the defined axis of rotation is permitted in respect of other reconstructed images of the image pairs used in Step 2. Hence the sole variable in the optimisation is, for example, the angle of rotation about the defined axis of rotation. For the result one obtains, for example, the optimum angle of rotation for the error correction about the defined axis.

An advantage of the previously described version is that in Step S1 no new reconstructed images have to be calculated. Thus computing time is saved. On the other hand, usually a single execution of Step S2 is adequate to determine the remaining position correction for one of the axes of rotation in the plane of the image of the comparison image (or parallel to it).

The flow diagram shown in FIG. 4 is divided into an upper and a lower part by a broken line. The upper part contains a special version of Step S1 in accordance with FIG. 3. The lower part contains Step S2 in accordance with FIG. 3. Reference is therefore made in part to FIG. 3.

In Step S5 three-dimensional image data of the patient is prepared, from which the reconstructed images are calculated in Step S6, for two image recording devices, which are prepared for further processing in Step S8a for the first image recording device and in Step S8b for the second image recording device. In Step S7a a comparison image of the first image recording device and in Step S7b a comparison image of the second image recording device are prepared for further processing.

In Step S9a the image pair with the largest mutual information is determined using an optimisation algorithm (e.g. a Downhill Simplex algorithm, which is applied to the negated value of the mutual image information of the image pair). In this, for example, merely the reconstructed image is changed in order to obtain new image pairs, and no distortion of the image content is permitted in the generation of the new images. Step S9b is executed in an appropriate way for the comparison image and the reconstructed image of the second image recording device.

In Step S10a the position correction parameters are determined from the optimisation in Step S9a In Step S10b the position correction parameters are determined from the optimisation in Step S9b. Thus there are two sets of correction parameters, from which in Step S11a or S11b, respectively, one set of correction parameters is calculated, for example in the coordinate system of the patient or in the coordinate system of a treatment table.

For a special case, in which the normals to the image planes of the image recording devices are perpendicular to the same axis of rotation of the arrangement (in particular perpendicular to the longitudinal axis of the treatment chamber) an optimisation is now carried out. Then in Step S13 a first common set of correction parameters is formed.

Since due to the special geometric arrangement of the image recording devices there is insufficient information for an unambiguous solution for the determination of the common sets of correction parameters, in Step S14a and S14b the correction parameters found in Step S13 are varied and optimized by repeating Steps S11a, S11b and Step S13 (for example, once more using a Downhill-Simplex optimisation algorithm). The optimisation minimizes the deviations in the evaluations of the two comparison images. Further, the deviation of the correction parameters determined from the two image recording devices is evaluated using an error measure.

Thus the error measure and the correction parameters are available in Step S15. A check is now made on the basis of the error measure to determine if the error is too large and therefore Steps S6 to S15 need to be repeated. If this is the case, then a geometrical transformation obtained from the correction parameters is executed in Step S16, so that in Step S6 reconstructed images are calculated corresponding to the corrected relative position of the patient and the radiation device.

If it is established in Step S15, that the error is not too large, then the procedure continues at Step S18, in which a check is made to ascertain if the following steps have already been executed. If this is the case, then the result of the position correction is established (Step S19) and the method ends at Step S20. If this is not the case, then in Step S21 the geometrical transformation obtained from the results of Steps S6 to S15 is carried out, so that in the previously described Step S2a the reconstructed image is calculated, commencing from the corrected relative position of the patient and the radiation device. At Step S2a there follows the likewise already described Step S2b, wherein these steps are repeated in the framework of the optimisation. As a result of the optimisation a further correction parameter is available in Step S4, which describes the rotation correction about the axis of rotation running parallel with the image planes of the two image recorders.

Step S16 now follows, in which in addition to the result of the position correction from Steps S6 to S15, the result of the rotation correction is also taken into account, so that in Step S6, after execution of both corrections (or the total resulting position correction) new reconstructed images are calculated. A new execution of the following steps then follows, at least up to Step S15. If the procedure again reaches Step S18, it is terminated as described above.

The invention claimed is:

1. A method for setting a relative position of a radiation device and of a patient, comprising the following steps:
   a) a two-dimensional comparison image is obtained, or has been obtained, by a comparison image recording device, wherein the comparison image corresponds to a current relative position of the patient and of the comparison image recording device;
   b) a two-dimensional image is reconstructed from a three-dimensional image data set of the patient;
   c) for a comparison image and a first reconstructed image, which form a first image pair and which corresponds to a first relative position of the patient and of the comparison image recording device, a measure for a mutual image information of the two images of the first image pair is determined, wherein the mutual image information is defined as that information, which one image contains about the other image of the image pair, or wherein the mutual image information is equivalent to the thus defined information;
   d) in order to obtain an amended image pair, at least one of the following three steps is performed:
      i) the comparison image is amended, without distortion of image content,
      ii) the reconstructed image is amended, without distortion of image content,
      iii) a second reconstructed image is reconstructed from the three-dimensional image data set of the patient, so that the second reconstructed image corresponds to a relative position of the patient and of the comparison image recording device which differs from the first relative position,
   resulting in the amended image pair comprising a comparison image and a reconstructed image so that at least one of the comparison image and reconstructed image of the amended image pair corresponds to another relative position of the patient and of the comparison image recording device, than the comparison image and the reconstructed image which form the first image pair;

e) the measure for the mutual image information is determined for the images of the amended image pair resulting from step d);

f) the two previous steps d) and e) are repeated using an optimisation algorithm, until an image pair is found having a maximum of the mutual image information;

g) by evaluating changes in the relative position of the patient and of the comparison image recording device in the images, which arise, or have arisen, starting from the first image pair and proceeding until the image pair having the maximum of the mutual image information is found, a geometrical transformation of the actual relative position of the patient and of the comparison image recording device or of another actual relative position or position of the patient is calculated and h) steps c) to g) are repeated, wherein the first reconstructed image is selected, such that it corresponds to a position of the patient or to a relative position of the patient and of the comparison image recording device which is obtained by modifying a previous position corresponding to the geometric transformation calculated in step g).

2. The method in accordance with claim 1, wherein in at least one iteration of step d) a second reconstructed image is reconstructed from the three-dimensional image data set of the patient, so that the second reconstructed image and the first reconstructed image correspond to a second and a first relative position of the patient and the comparison image recording device, and wherein the second relative position can be transformed into the first relative position through a rotation of the patient about a defined axis of rotation.

3. The method in accordance with claim 2, wherein steps d) and e) are repeated, in order, in step f), to find the image pair with the maximum of the mutual image information by using an optimisation algorithm, wherein the second reconstructed image corresponds to a further relative position of the patient and of the comparison image recording device, and wherein the further relative position can be transformed into the first relative position through a rotational motion of the patient about the defined axis of rotation.

4. The method in accordance with claim 1, wherein two comparison images, which have been taken by different comparison image recording devices, are assigned to, in each case, one reconstructed image so as to form two image pairs and, in step c), the measure for the mutual image information of the two image pairs is determined;

the comparison image recording devices take comparison images of the patient from different directions;

in step d), for each of the two image pairs, the comparison image and the reconstructed image is modified by a rotation about an axis perpendicular to the plane of the image and by a shift in the image plane, so that at least one of the images of the respective image pair corresponds to another relative position of the patient and the comparison image recording device;

steps e) and f) are executed for each of the two image pairs;

in the execution of step g) optimisation results from step f) are taken into account for the two image pairs.

5. The method in accordance with claim 4, wherein the comparison image recording devices take comparison images of the patient from directions at right angles to each other and wherein in the execution of step g) the calculated geometric transformation is iteratively improved by repeating the calculation.

6. An arrangement for setting of a relative position of a radiation device of a patient, wherein the arrangement comprises an image data evaluation device, which is connected to an interface for transfer of image data, wherein the image data evaluation device is adapted to process at least one two-dimensional comparison image and to process reconstructed images, wherein the comparison image is obtained, or has been obtained, using a comparison image recording device and wherein the comparison image corresponds to a current relative position of the patient and of the comparison image recording device, wherein the reconstructed images are two-dimensional images reconstructed from a three-dimensional image data set of the patient, wherein the reconstructed images respectively simulate an image taken with the comparison image recording device, which corresponds to an estimated or assumed relative position of the patient and of the comparison image recording device;

the image data evaluation device has a determination device (6), which is adapted to determine a measure for a mutual information of a comparison image and of a first reconstructed image, which form an image pair, wherein the mutual image information is defined as that information, which one image of the image pair contains about the other image of the same image pair, or wherein the mutual image information is equivalent to the thus defined information;

the image data evaluation device has an image processing device, which is adapted to amend the comparison image by performing at least one of the following three steps:

i) the comparison image is amended without distortion of image content, ii) the reconstructed image is amended, without distortion of image content, iii) a second reconstructed image is reconstructed from the three-dimensional image data set of the patient, so that the second reconstructed image corresponds to a relative position of the patient and of the comparison image recording device which differs from the first relative position, resulting in an amended image pair comprising a comparison image and a reconstructed image so that at least one of the comparison image and the reconstructed image of the amended image pair corresponds to another relative position of the patient and of the comparison image recording device than the comparison image and the reconstructed image which form the first image pair; so that the second reconstructed image of the amended image pair corresponds to a second relative position of the patient and of the comparison image recording device which differs from the first relative position, a control device is provided, which is connected to the determination device and the image processing device and which is adapted to control the operation of the determination device and the image processing device in such a way, that the measure of the mutual image information is repeatedly determined in each case for an image pair which is provided by the image processing device and that, by using an optimisation algorithm, a maximum of the mutual image information is found for a corresponding resulting image pair;

a transformation calculation device is provided to evaluate changes in the relative position of the patient and of the comparison image recording device in correspondence with the images, which arise or have arisen, proceeding from a first image pair up until the resulting image pair is found, wherein the transformation calculation device is adapted to calculate a geometrical transformation of an actual relative position of the patient and of the comparison image recording device or another actual relative position or position of the patient; wherein the control device is adapted to control the operation of the arrangement in such a way, that proceeding from a newly calculated first reconstructed image and for the corresponding comparison image, the geometrical transformation is repeatedly calculated, wherein the first reconstructed image is selected in such a way, that it corresponds to the relative position or position as modified by the geometrical transformation.

7. The arrangement in accordance with claim 6, wherein the arrangement has an image data memory, in which the three-dimensional data is stored, wherein the image data memory is connected with the image data evaluation device.

* * * * *